US010699807B2

(12) United States Patent
Kitagawa (10) Patent No.: US 10,699,807 B2
(45) Date of Patent: Jun. 30, 2020

(54) NURSE CALL SYSTEM (71) Applicant: AIPHONE CO., LTD., Nagoya-shi, Aichi (JP)

(72) Inventor: Kazumi Kitagawa, Nagoya (JP)

(73) Assignee: AIPHONE CO., LTD., Nagoya-Shi, Aichi (JP)

(*) Notice: Subject to any disclaimer, the term of this patent is extended or adjusted under 35 U.S.C. 154(b) by 682 days.

(21) Appl. No.: 15/129,292

(22) PCT Filed: Feb. 26, 2015

(86) PCT No.: PCT/JP2015/055625
§ 371 (c)(1),
(2) Date: Sep. 26, 2016

(87) PCT Pub. No.: WO2015/146457
PCT Pub. Date: Oct. 1, 2015

(65) Prior Publication Data
US 2017/0116377 A1 Apr. 27, 2017

(30) Foreign Application Priority Data

Mar. 27, 2014 (JP) ................................. 2014-065925

(51) Int. Cl.
G16H 40/20 (2018.01)
G06Q 50/22 (2018.01)
A61G 10/00 (2006.01)

(52) U.S. Cl.
CPC ............ *G16H 40/20* (2018.01); *G06Q 50/22* (2013.01); *A61G 10/00* (2013.01)

(58) Field of Classification Search
CPC ......... G16H 40/20; G06Q 50/22; A61G 10/00
See application file for complete search history.

(56) References Cited

U.S. PATENT DOCUMENTS

2005/0075904 A1* 4/2005 Wager .................... G06Q 10/10
705/2
2006/0049936 A1* 3/2006 Collins, Jr. ........... A61B 5/1115
340/539.11

(Continued)

FOREIGN PATENT DOCUMENTS

CN 101322660 A 12/2008
CN 101404926 A 4/2009

(Continued)

OTHER PUBLICATIONS

Office Action for Japanese Patent Application No. 2014-065925 dated Aug. 29, 2017; 10 pages. English translation provided.

(Continued)

Primary Examiner — Michael Tomaszewski
Assistant Examiner — Mohmad Muqueeth
(74) Attorney, Agent, or Firm — Procopio, Cory, Hargreaves & Savitch LLP (57) ABSTRACT A nurse call system according to the present invention includes a nurse call master unit (3) which includes a first display part (31); a patient information memory unit (52a) which stores patient information containing at least names of patients and person-in-charge information representing nurses each in charge of one or more of the patients; a working information memory unit (38a) which stores working information of the nurses for each date and each working time zone; and a display control unit (36) which can display a plurality of the patients and the individual nurses in charge of the plurality of patients in a next or succeeding working time zone simultaneously on the first display part (31), in a manner of associating each of the plurality of patients with one of the nurses, based on the patient and working information.

8 Claims, 7 Drawing Sheets (56) References Cited

U.S. PATENT DOCUMENTS

| | | | |
|---|---|---|---|
| 2009/0100364 A1 | 4/2009 | Kinoshita et al. | |
| 2012/0041776 A1 | 2/2012 | Minato et al. | |
| 2012/0253836 A1 | 10/2012 | Nolte et al. | |
| 2012/0323595 A1 | 12/2012 | Hawkins et al. | |
| 2014/0285490 A1* | 9/2014 | Gilger ................ | G06T 11/206 345/440 |

FOREIGN PATENT DOCUMENTS

| | | |
|---|---|---|
| CN | 102375929 A | 3/2012 |
| CN | 102496133 A | 6/2012 |
| JP | 2001237959 A | 8/2001 |
| JP | 2005244581 A | 9/2005 |
| JP | 2005349020 A | 12/2005 |
| JP | 2006130083 A | 5/2006 |
| JP | 2007-257351 A | 10/2007 |
| JP | 2011-030731 A | 2/2011 |
| JP | 2011078640 A | 4/2011 |
| JP | 2013-121387 A | 6/2013 |
| JP | 2013150133 A | 8/2013 |
| JP | 2014-042711 A | 3/2014 |

OTHER PUBLICATIONS

Notification of First Office Action for CN App No. 201580016370.7 dated May 23, 2018, 18 pgs.
Extended European Search Report for EP15770019 dated Oct. 16, 2017, 9 pages.
International Search Report and Written Opinion for PCT App No. PCT/JP2015/055625 dated Jun. 2, 2015, 6 pgs.

* cited by examiner

NURSE CALL SYSTEM

CROSS-REFERENCE TO RELATED APPLICATIONS

This application is a U.S. National Stage entry of PCT Application No. PCT/JP2015/055625, filed on Feb. 26, 2015, which claims priority to JP Application No. 2014-065925, filed Mar. 27, 2014. The contents of the foregoing are incorporated by reference.

TECHNICAL FIELD

The present invention relates to a nurse call system.

BACKGROUND ART

There has been proposed a nurse call system which includes a nurse call master unit having a display capable of displaying patient information (see Patent Document 1).

A nurse manager such as a chief nursing officer or a chief nurse in a hospital can consider assignment of new inpatients to nurses while confirming patient information such as scheduled date of hospitalization and previous symptom history for each new inpatient, utilizing the system described in the patent document 1, etc. . . . .

PRIOR ART DOCUMENT

Patent Document

Patent Document 1: JP-A-2007-257351

SUMMARY OF INVENTION

Problems to be Solved by Invention

However, according to the technique utilizing such the system of the related art, there arises a case that assignment of a nursing load originally intended by the nurse manager is not achieved. For example, there arises a case that the nursing loads assigned to individual nurses are not sufficiently equalized and so the nursing load concentrates on a particular nurse. Such the situation may badly influence on efficiency and quality of nursing service in the entirety of a hospital.

Accordingly an object of the present invention is to provide a nurse call system which can improve efficiency and quality of nursing service in the entirety of a hospital.

Means for Solving Problems

In order to attain the aforesaid object, according to the present invention, there is provided a nurse call system which includes:

a nurse call master unit which includes a first display part;

a patient information memory unit which stores patient information containing at least names of patients and person-in-charge information representing nurses each in charge of one or more of the patients;

a working information memory unit which stores working information of the nurses for each day and each working time zone; and a display control unit which can display a plurality of the patients and the nurses each in charge of one or more of the plurality of patients in a next or succeeding working time zone simultaneously on the first display part, in a display mode of associating each of the plurality of patients with one of the nurses, based on the patient information and the working information.

According to this configuration, the plurality of patients and the nurses each in charge of one or more of the plurality of patients in the next or succeeding working time zone are simultaneously displayed on the first display part, in the display mode of associating each of the plurality of patients with one of the nurses. Thus, by looking at the first display part, a nurse manager can easily understand nursing loads supposed to be assigned to the individual nurses in the next or succeeding working time zone under a currently-scheduled nursing system (assignment of work to the individual nurses) in a comparison manner. Therefore the nurse manager can easily reorganize the nursing system so that the assignment of nursing load to the individual nurses in the next or succeeding working time zone becomes intended assignment (even assignment, for example). As a result, unintentional assignment, for example, concentration of the nursing load on a particular nurse can be suppressed occurring, and hence efficiency and quality of nursing service in the entirety of a hospital can be improved.

In the nurse call system according to the present invention, the nurse call master unit may include an operation part which can change the nurse in charge of the patient displayed on the first display part, in a state where the plurality of patients and the nurses each in charge of one or more of the plurality of patients in the next or succeeding working time zone are simultaneously displayed on the first display part, in the display mode of associating each of the plurality of patients with one of the nurses.

According to this configuration, the nurse manager can operate the operation part and change the nurses in charge of the individual patients in the next or succeeding working time zone while looking at the first display part of the nurse call master unit. Thus efficiency of an organization operation of reconsidering and reorganizing the nursing system can be improved.

The nurse call system according to the present invention may further includes a layout information memory unit which stores layout information of individual hospital rooms in a predetermined area of a hospital, wherein the patient information may further contain hospital room information of the individual patients, and wherein the display control unit may be able to display a layout screen indicating a layout of the individual hospital rooms in the predetermined area of the hospital on the first display part based on the layout information, and the display control unit may also be able to display the plurality of patients, the nurses each in charge of one or more of the plurality of patients and the hospital rooms for the plurality of patients in the next or succeeding working time zone simultaneously over the layout screen on the first display part, in a display mode of associating each of the plurality of patients with one of the nurses and one of the hospital rooms, based on the patient information and the working information.

According to this configuration, the plurality of patients, the nurses each in charge of one or more of the plurality of patients and the hospital rooms for the plurality of patients in the next or succeeding working time zone are simultaneously displayed over the layout screen indicating the layout of the hospital rooms in the predetermined area of the hospital on the first display part, in the display mode of associating each of the plurality of patients with one of the nurses and one of the hospital rooms. Thus, by looking at the first display part, the nurse manager can easily understand nursing loads supposed to be assigned to individual nurses, also in view of the positional relation of hospital rooms, in the next or succeeding working time zone under the currently-scheduled nursing system in a comparison manner. Consequently the nurse manager can further easily reorganize the nursing system so that the assignment of nursing load to the individual nurses in the next or succeeding working time zone becomes the intended assignment.

In the nurse call system according to the present invention, the patient information memory unit may store patient information of patients now being hospitalized and patient information of patients scheduled to be hospitalized.

According to this configuration, as the nursing system can be reorganized also in view of the patients scheduled to be hospitalized, the nurse manager can easily consider the nursing system in detail so that the assignment of nursing load to the individual nurses becomes the intended assignment.

In the nurse call system according to the present invention, the display control unit may be able to emphatically display the patient information of patients assigned to a particular one of the nurses, in the state where the plurality of patients and the nurses each in charge of one or more of the plurality of patients in the next or succeeding working time zone are simultaneously displayed on the first display part, in the display mode of associating each of the plurality of patients with one of the nurses.

According to this configuration, as the patient information of patients assigned to a particular nurse can be easily recognized, the nurse manager can easily consider the nursing system so that the assignment of nursing load to the individual nurses in the next or succeeding working time zone becomes the intended assignment.

In the nurse call system according to the present invention, the operation part may be able to select the patient information of a particular one of the patients and input a patient memo, in the state where the plurality of patients and the nurses each in charge of one or more of the plurality of patients in the next or succeeding working time zone are simultaneously displayed on the first display part, in the display mode of associating each of the plurality of patients with one of the nurses, and the patient memo may be reflected on the patient information of all of the other patients assigned to the nurse in charge of the particular patient.

According to this configuration, the patient memo inputted concerning the patient information of the particular patient is reflected on the patient information of all of the other patients assigned to the nurse in charge of the particular patient. Thus an operation of inputting the patient memo can be simplified and input omission of the memo can be prevented. Further, as the nurse manager can reconsider the current nursing system also in view of the contents of nurse memo, consideration for achieving the intended assignment of nursing load can be further facilitated.

The nurse call system according to the present invention may further include a nurse call slave unit which can communicate with the nurse call master unit, wherein the nurse call master unit may include a second display part, and wherein the display control unit may display the patient information of one of the patients who is calling from the nurse call slave unit, in the state where the plurality of patients and the nurses each in charge of one or more of the plurality of patients in the next or succeeding working time zone are simultaneously displayed on the first display part, in the display mode of associating each of the plurality of patients with one of the nurses.

According to this configuration, as the patient information of a patient originating a nurse call is displayed on the second display part, a work of quickly dealing with the patient who originated the nurse call can be performed together with a work of displaying the next or succeeding working time zone on the first display part and considering or changing the nursing system.

The nurse call system according to the present invention may further include a display unit which can communicate with the display control unit and includes a third display part, wherein the display control unit may be able to display a plurality of the patients and the nurses each in charge of one or more of the plurality of patients in a current working time zone simultaneously on the third display part in a display mode of associating each of the plurality of patients with one of the nurses, in the state where the plurality of patients and the nurses each in charge of one or more of the plurality of patients in the next or succeeding working time zone are simultaneously displayed on the first display part in the display mode of associating each of the plurality of patients with one of the nurses.

According to this configuration, the nursing system can be, for example, considered or changed by displaying the next or succeeding working time zone on the first display part, in the state where the plurality of patients and the nurses each in charge of one or more of the plurality of patients in the current working time zone are simultaneously displayed on the third display part in the display mode of associating each of the plurality of patients with one of the nurses.

In the nurse call system according to the present invention, the operation part may be able to input a working time zone memo with respect to information displayed on the first display part, in the state where the plurality of patients and the nurses each in charge of one or more of the plurality of patients in the next or succeeding working time zone are simultaneously displayed on the first display part, in the display mode of associating each of the plurality of patients with one of the nurses, and the working time zone memo may be displayed on the first display part only in the state where the plurality of patients and the nurses each in charge of one or more of the plurality of patients in the next or succeeding working time zone are simultaneously displayed on the first display part, in the display mode of associating each of the plurality of patients with one of the nurses.

According to this configuration, as the nurse manager can reconsider the current nursing system also in view of the contents of working time zone memo, consideration for achieving the intended assignment of nursing load can be further facilitated.

Advantageous Effects of Invention

According to the nurse call system of the present invention, efficiency and quality of nursing service in the entirety of a hospital can be improved.

EMBODIMENTS OF INVENTION

Hereinafter a nurse call system according to an embodiment of the present invention will be explained with reference to drawings.

Figure 1:
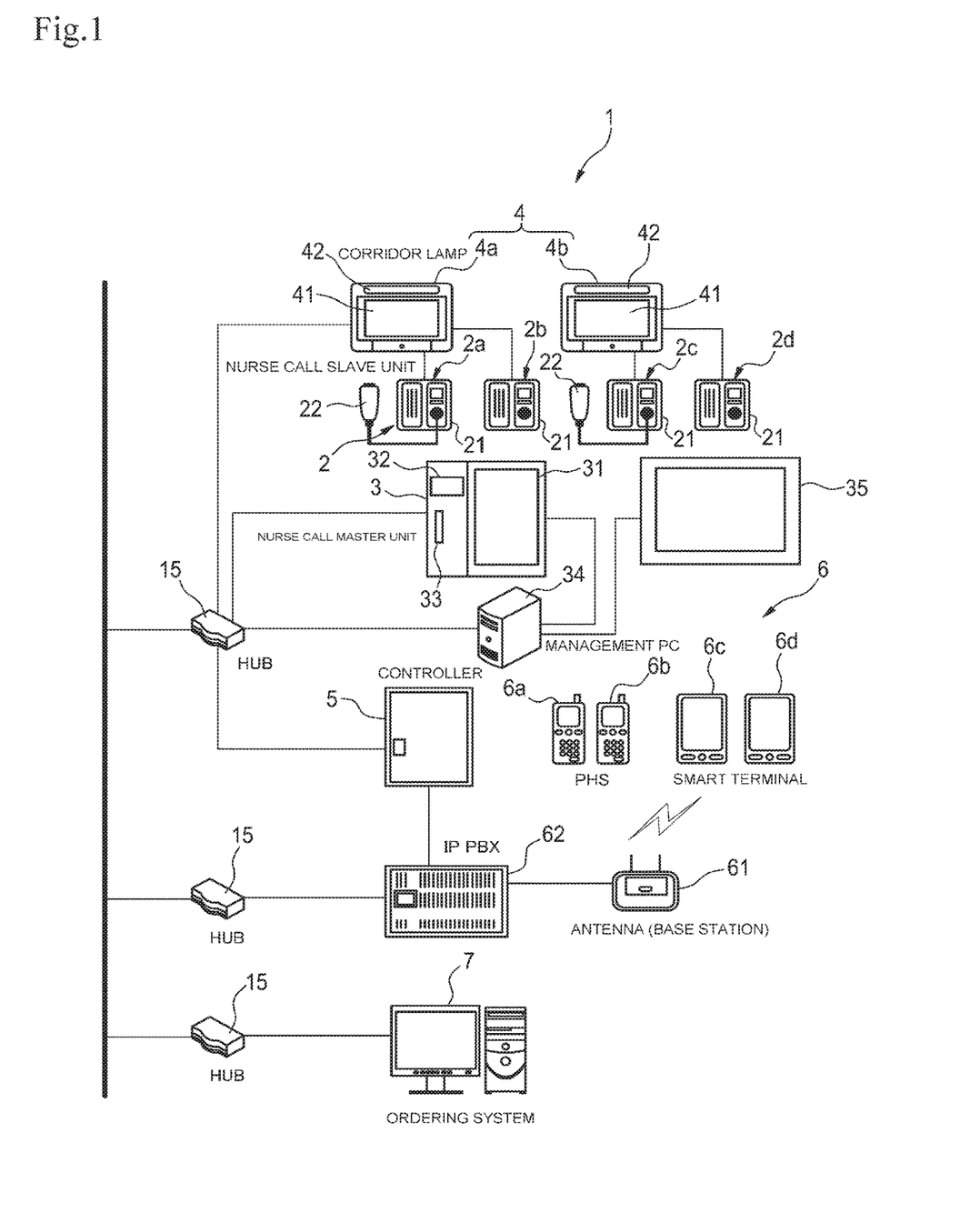
FIG. 1 A configuration diagram of a nurse call system according to an embodiment.

FIG. 1 is a configuration diagram of the nurse call system 1 according to the embodiment.

As shown in FIG. 1, the nurse call system 1 includes a plurality of (four in this example) nurse call slave units 2a, 2b, 2c and 2d (hereinafter referred to as the nurse call slave unit 2 in a case of being collectively referred), a nurse call master unit 3, a sub-monitor 35, a plurality of (two in this example) corridor lamp 4a and 4b (hereinafter referred to as the corridor lamp 4 in a case of being collectively referred), a controller 5, a plurality of (four in this example) mobile terminals 6a, 6b, 6c and 6d (hereinafter referred to as the mobile terminal 6 in a case of being collectively referred), a base station 61 and an exchange 62. The nurse call system 1 is connected to an ordering system 7 via a hub (HUB) 15.

The nurse call system 1 is installed in, for example, a medical care facility such as a hospital accommodating patients.

The nurse call slave unit 2 is used for a patient to call and communicate with a nurse and installed at every bed within each hospital room. The nurse call slave unit 2 includes a plate slave unit 21 and a handset 22. The plate slave unit 21 includes a microphone and a speaker and is installed at a wall surface above the bed of each patient. The microphone and the speaker are used for performing communication mutually between a patient and a nurse. The handset 22 includes a call button and is connected to the plate slave unit 21 via a cable. The call button is a button used for a patient within a hospital room to call a nurse. The nurse call slave unit 2 is connected to the corridor lamp 4 via a communication cable.

The corridor lamp 4 detects a call from each patient and notifies the call to the outside of the hospital room. The corridor lamp is installed near the inlet of the hospital room. The corridor lamp 4 in this example is connected to the controller 5 via the hub 15. In this example, the corridor lamp 4 is provided with a liquid crystal display part 41 and configured to, when a call is transmitted from the nurse call slave unit 2, display patient information such as name of a patient who has originated the call on the liquid crystal display part 41. Further, when a call is transmitted from the nurse call slave unit 2, the corridor lamp 4 is configured to, for example, blink a display lamp 42 provided at the corridor lamp 4.

The nurse call master unit 3 has a function of enabling a nurse to communicate with a patient in response to a call from the patient and displaying information of patients, nurses, etc. The nurse call master unit 3 is installed at a common space such as a staff station within the facility. The nurse call master unit 3 includes a large-sized monitor (an example of the first display part) 31, a small-sized monitor (an example of the second display part) 32 and a communication section 33.

The large-sized monitor 31 is configured by a vertically-long touch panel screen of 24-inch model, for example, and can also function as an operation part of the nurse call master unit 3.

The small-sized monitor 32 is configured by a horizontally-long touch panel screen of 7-inch model, for example. For example, when a call by a patient is transmitted from the nurse call slave unit 2, the small-sized monitor 32 displays patient information such as name and bed No. of the patient who originated the call.

The communication section 33 includes a speaker for outputting a ringing tone and voice of a patient, and a communication part for enabling a nurse to communicate with the patient in response to the call from the patient.

A CPU 36 (see FIG. 3) of the nurse call master unit 3 is connected to the sub-monitor (an example of a display device having the third display part) 35 via a management PC 34 so as to be able to perform communication. The sub-monitor 35 includes a liquid crystal display part larger than the large-sized monitor 31 of the nurse call master unit 3, for example, and is installed at a wall surface of the staff station, for example. The management PC 34 performs switching control between screens displayed on the large-sized monitor 31 and the sub-monitor 35, for example. Each of the nurse call master unit 3 and the management PC 34 is connected to the controller 5 via the hub 15.

The controller 5 is installed as a relay and performs calling control, communication control, etc. of each of the constituent elements connected thereto. The controller 5 is connected to the corridor lamps 4, the nurse call master unit 3, the management PC 34, an exchange (IP PBX) 62 described later and the ordering system 7 via the hubs 15 and the communication cables.

The mobile terminal 6 is used for notifying a call from the nurse call slave unit 2 and communicating with a patient in response to the call. The mobile terminals are carried by individual nurses. The mobile terminal 6 is provided with a display screen which displays hospital room No. bed No. name, etc. of a patient as a caller in response to the call from the nurse call slave unit 2. For example, PHSs 6a, 6b, smart terminals 6c, 6d, etc. are used as the mobile terminals 6. The mobile terminals 6a, 6b, 6c, 6d have respective terminal Nos.

The base station 61 performs radio communication with the mobile terminals 6. The base stations are installed near the staff station and at locations apart from the staff station within the facility with a predetermined interval therebetween. The exchange 62 (for example, IP PBX or the like) connects between the mobile terminals 6 and the nurse call slave units 2 and is installed within the staff station or at the common space within the facility. The exchange 62 is connected to the controller 5 via the communication cable. Further the exchange 62 is connected to the nurse call slave units 2 via the hubs 15.

Figure 2:
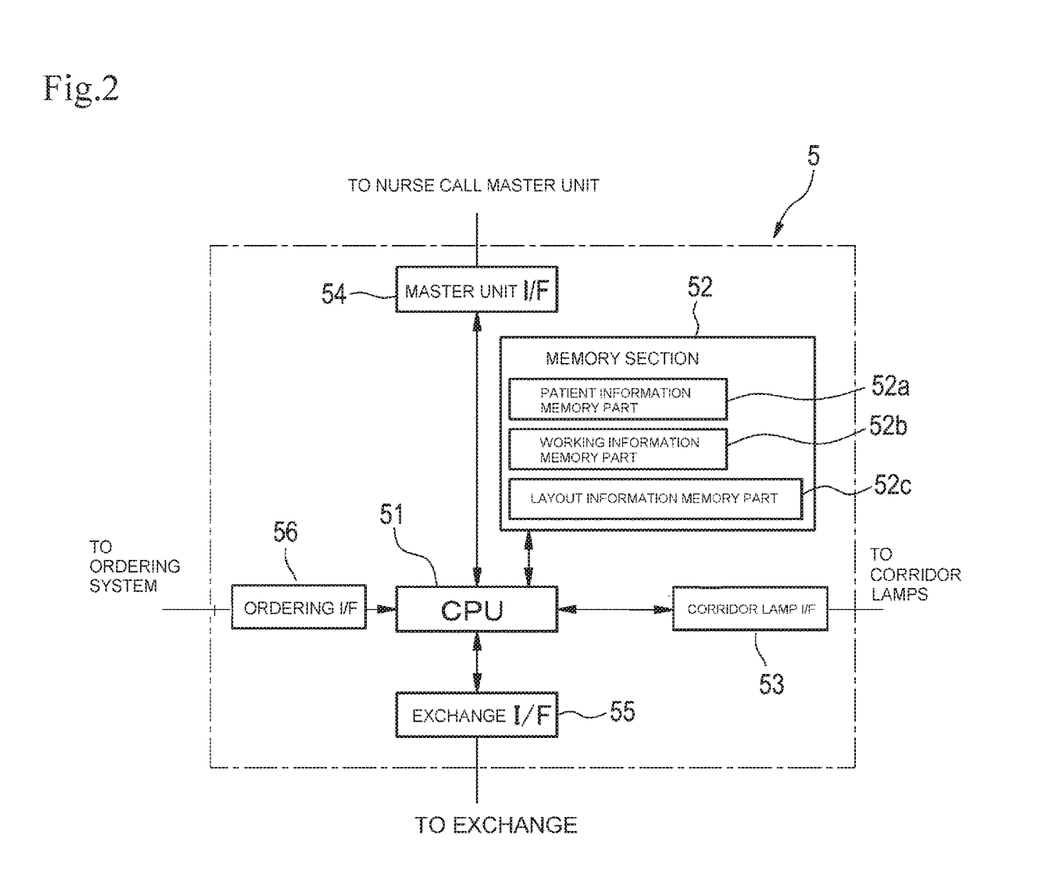
FIG. 2 A functional block diagram of a controller in the nurse call system shown in FIG. 1.

The ordering system 7 collectively manages information relating to the hospital including the patient information of individual patients and is installed at a predetermined location such as a management room of the facility, for example, FIG. 2 is a functional block diagram of the controller 5.

As shown in FIG. 2, the controller 5 includes a CPU 51, a memory section 52 connected to the CPU 51, a corridor lamp interface circuit (hereinafter the interface circuit is referred to as an "I/F") 53, a master unit I/F 54, an exchange I/F 55 and an ordering I/F 56.

The corridor lamp I/F 53 constitutes a communication part for forming a signal transmission path to the corridor lamps 4. The master unit I/F 54 constitutes a communication part for forming a signal transmission path to the nurse call master unit 3. The exchange I/F 55 constitutes a communication part for forming a signal transmission path to the exchange 62. The ordering I/F 56 constitutes a communication part for forming a signal transmission path to the ordering system 7. The ordering I/F also acts as a circuit for receiving information managed by the ordering system 7.

The memory section 52 is provided with a patient information memory part 52a, a working information memory part 52b and a layout information memory part 52c. The patient information memory part 52a stores the patient information which is constituted by, for each patient currently being hospitalized, hospitalization date, scheduled discharging date from the hospital, name, sex, age, person-in-charge information containing main nurse in charge and assistant nurse in charge, doctor in charge, hospital room No., bed No., infection information, aid section, presence/non-presence of dietary restrictions, necessity degree of nursing, medication information, etc. Further the patient information memory part 52a stores the patient information for each patient scheduled to be hospitalized as well as the patient information for each patient currently being hospitalized. In this example, the patient information is, for example, periodically transmitted from the ordering system 7 and stored in the patient information memory part 52a.

The working information memory part 52b stores working information for each nurse. The working information is constituted by information concerning attendance, for example, every month for each nurse, working dates (containing scheduled working dates), working time zones (day shift, night shift and quasi-night shift in a case of three-shift system), holidays (containing scheduled holidays), etc. In this example, the working information is, for example, periodically transmitted from the ordering system 7 and stored in the working information memory part 52b.

The layout information memory part 52c stores layout information representing arrangements of hospital rooms in individual predetermined areas (particular hospital wards, floors, etc.) of the hospital. The layout information also includes information for specifying the hospital room No. of each hospital room and the bed No. of each patient. By associating the layout information with the hospital room information and the bed No. of each patient contained in the patient information, each patient being hospitalized can be related to the location in the predetermined area and the hospital room.

The CPU 51 performs, for example, management of transmission/reception, etc. of the information stored in the memory section 52, specifying of the mobile terminal 6 with respect to a call from the nurse call slave unit 2, and so on. In the case of specifying the mobile terminal 6, an association table between the nurses in charge and the mobile terminals 6 carried by the respective nurses is used.

Figure 3:
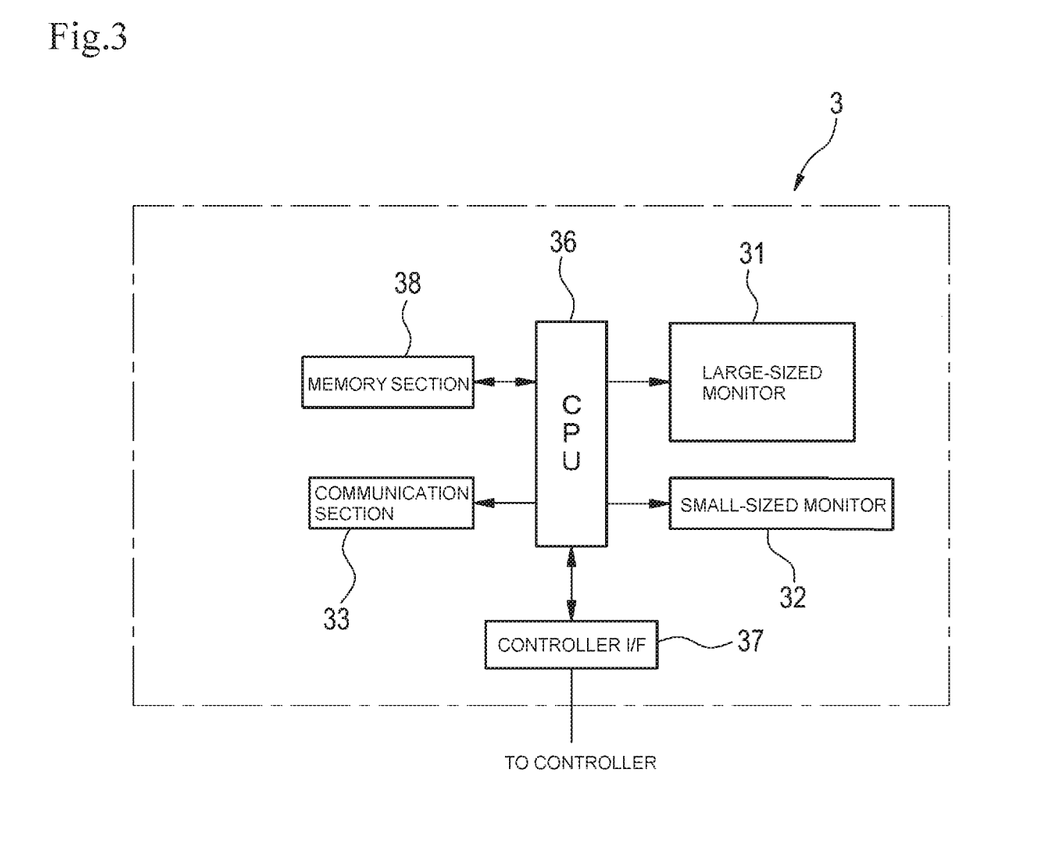
FIG. 3 A functional block diagram of a nurse call master unit in the nurse call system shown in FIG. 1.

FIG. 3 is a functional block diagram of the nurse call master unit 3.

As shown in FIG. 3, the nurse call master unit 3 includes a CPU (an example of a display control unit) 36, a controller I/F 37 and a memory section 38. The CPU 36 is connected to the large-sized monitor 31, the small-sized monitor 32 and the communication section 33 and controls respective operations thereof.

The controller I/F 37 constitutes a communication part for forming a signal transmission path to the controller 5.

The memory section 38 stores the patient information, the working information and the layout information stored in the memory section 52 of the controller 5. In this example, these information is, for example, periodically transmitted from the controller 5 and stored in the memory section 52.

The CPU 36 performs, for example, a processing of forming a screen displayed on the large-sized monitor 31 based on the patient information, the working information and the layout information stored in the memory section 38. Further, for example, when a call by a patient is transmitted from the nurse call slave unit 2, the CPU 36 performs control of displaying the patient information of the patient as the caller on the small-sized monitor 32 or the sub-monitor 35.

Next, an example of a screen displaying a current nursing system on the large-sized monitor 31 of the nurse call master unit 3 will be explained with reference to FIG. 4.

Figure 4:
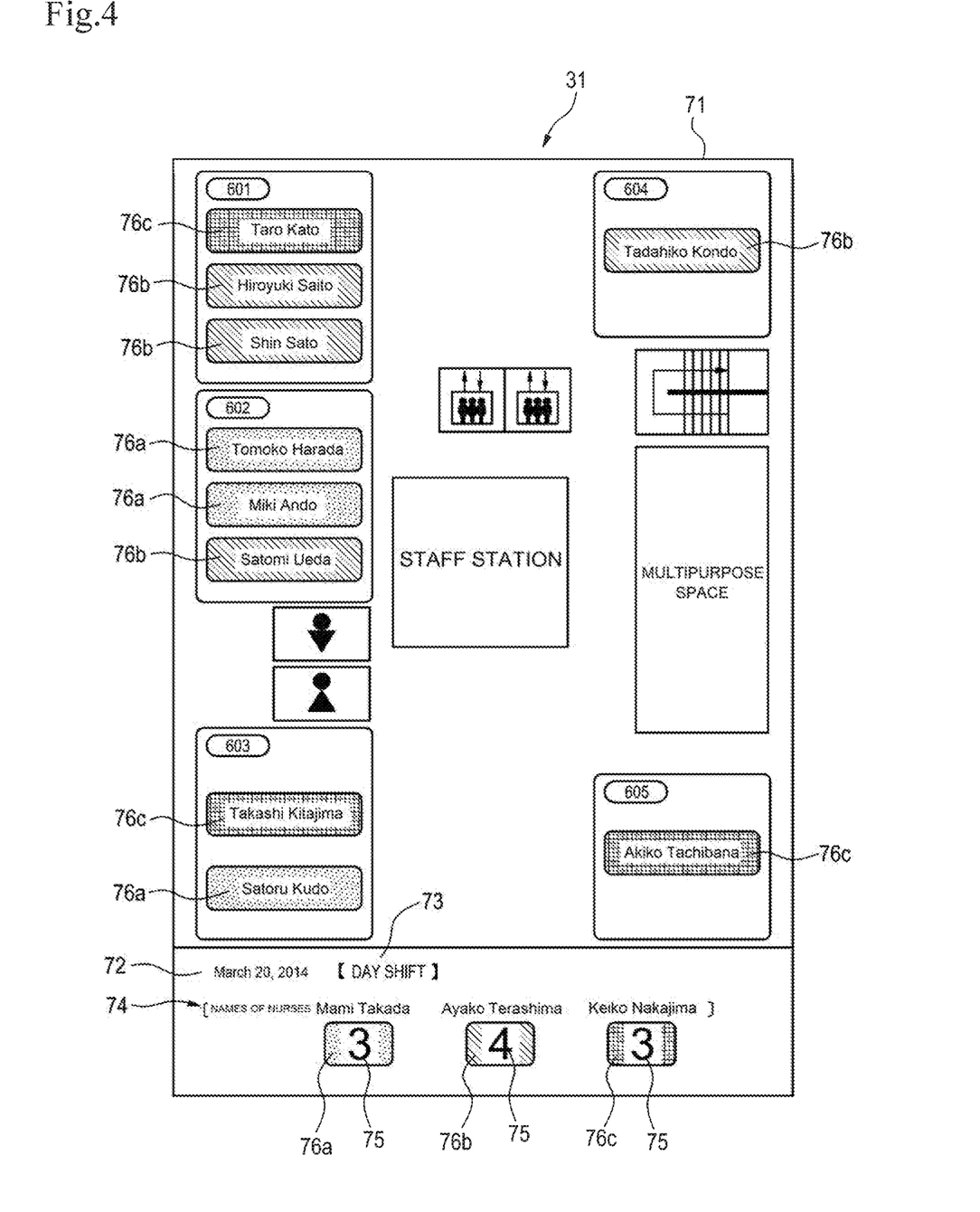
FIG. 4 A diagram illustrating an example of a layout screen displayed on the nurse call master unit.

As shown in FIG. 4, the large-sized monitor 31 displays a layout screen 71 illustrating a layout of individual hospital rooms in the predetermined area (for example, medical ward) of the hospital. The CPU 36 of the nurse call master unit 3 prepares this layout screen 71 based on the layout information stored in the memory section 38. In this layout screen 71, the staff station is displayed at the center of the screen, and hospital rooms 601 to 603 are schematically displayed sequentially by respective indication frames of almost rectangular shape from the upper left portion toward the lower left portion of the screen. Similarly hospital rooms 604 and 605 are displayed at the upper and lower right portions of the screen, respectively. Rest rooms are displayed between the hospital rooms 602 and 603, and a multipurpose space is displayed at the right side of the staff station on this screen.

Further names of patients allocated with inpatient's beds in the hospital rooms are displayed within the respective indication frames of almost rectangular shape of the hospital rooms 601 to 605 displayed on the layout screen 71. For example, the CPU 36 associates the hospital room Nos. and the bed Nos. of the patients contained in the patient information with the hospital room Nos. and the bed Nos. contained in the layout information to form an association table. Then the CU performs, using this association table, control of displaying the names of patients within the respective indication frames of the hospital rooms displayed on the layout screen 71.

Further, information relating to nurses in charge is displayed at the lower portion of the layout screen 71. Specifically, in an indication frame at the lower portion of the layout screen 71, a symbol 72 indicates a display part of today's date (Mar. 20, 2014) and a symbol 73 indicates a display part of a working time zone (day shift in this screen).

Further, a symbol 74 indicates a display part of the names (Mami Takada, Ayako Terashima, Keiko Nakajima) of nurses in charge of the patients displayed on the layout screen 71. A symbol 75 indicates a display part of the number of the patients assigned to the individual nurse. Symbols 76a to 76c indicate individual hatching patterns each applied to a region surrounding the number of the patients assigned to the associated nurse. These hatching patterns are also applied to the insides of indication frames surrounding the names of the patients assigned to the associated nurses. In place of applying the different hatching patterns to the indication frames, different optional colors may be applied to the indication frames.

Specifically the hatching pattern 76a same as the hatching pattern 76a, applied to the inside of an indication frame surrounding the number "3" of the patients assigned to the nurse Mami Takada, is also applied to the inside of each of indication frames respectively surrounding the names of three patients (Tomoko Harada, Miki Aodoh, Satoru Kudo)

assigned to the nurse Mami Takada. This is also applied to each of the nurse Ayako Terashima and the nurse Keiko Nakajima.

In this manner, concerning the layout screen 71 in this example, the names of patients and the names of nurses in charge of these patients at the current working time zone (day shift on Mar. 20, 2014) are simultaneously displayed on the large-sized monitor 31, in a display mode that the names of nurses in charge of the patients are associated with the names of these patients by the corresponding hatching patterns 76a to 76c. This is achieved by operating the CPU 36 of the nurse call master unit 3 so as to perform a processing of applying the same hatching pattern to the insides of the associated indication frames on the layout screen 71 which is prepared based on the layout information, using the names of patients contained in the patient and person-in-charge information.

Next, an operation at the time of reconsidering and organizing the nursing system at the next or succeeding working time zone will be explained with reference to FIGS. 4 to 6.

By looking at the layout screen 71 shown in FIG. 4, each of the nurse manager and the nurses in charge can confirm the nursing system (assignment of work to the individual nurses in charge) at the current working time zone (day shift on Mar. 20, 2014).

Figure 5:
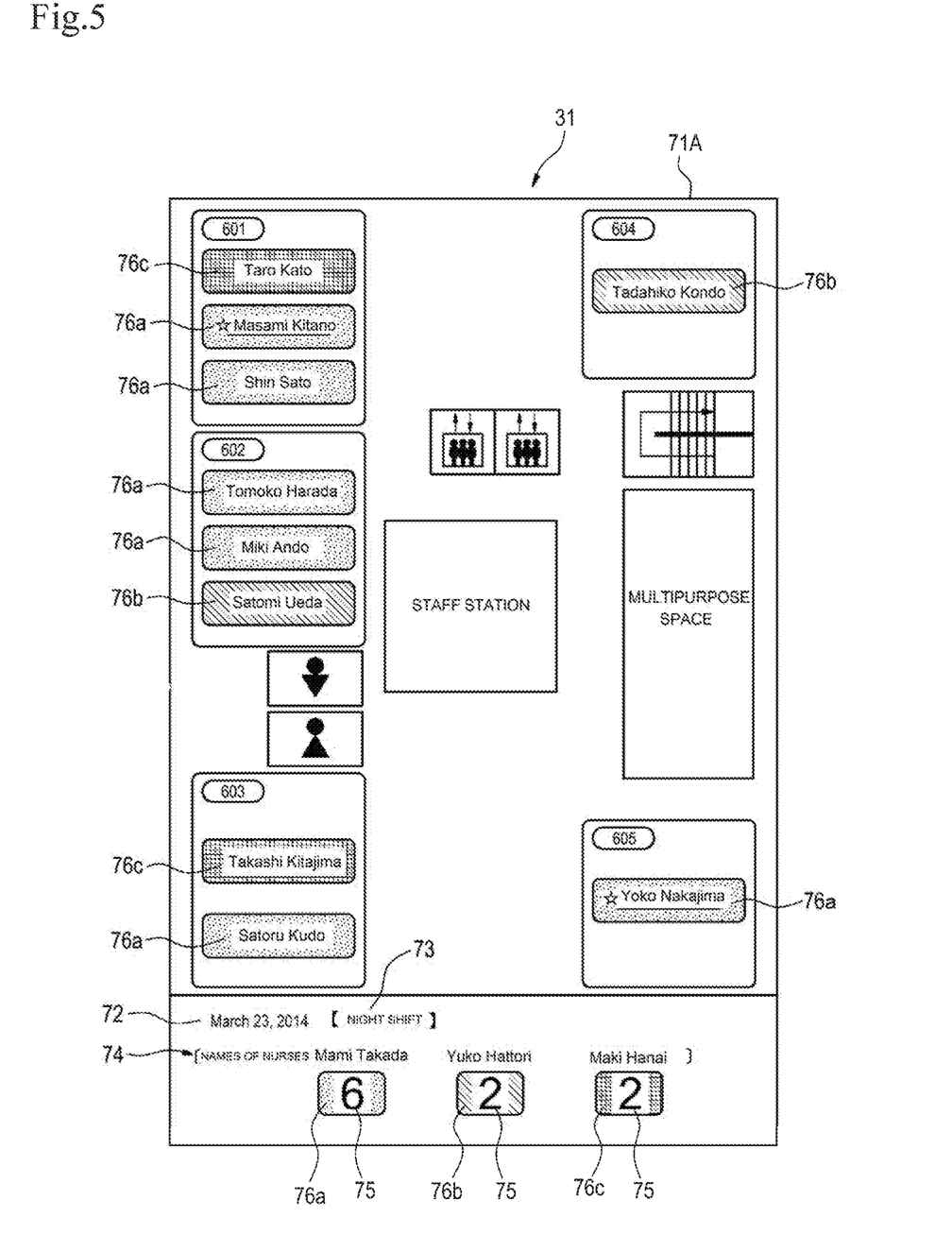
FIG. 5 A diagram illustrating an example of a layout screen in the next or succeeding working time zone.

For example, the nurse manager touches the display part 72 of today's date (Mar. 20, 2014) and the display part 73 of the working time zone (day shift in this screen) in the layout screen 71 displayed on the touch panel screen, thereby selecting the next or succeeding working time zone (night shift on Mar. 23, 2014 which is three days later from today) as shown in FIG. 5.

In this case, a layout screen 71A at the night shift on Mar. 23, 2014 is displayed on the large-sized monitor 31 of the nurse call master unit 3, as shown in FIG. 5.

In the layout screen 71A, names of patients, names of nurses in charge and the numbers of the patients assigned to the individual nurses at the night shift on Mar. 23, 2014 are displayed. Specifically, as shown in FIGS. 4 and 5, name of one of the patients of the room No. 601 is changed from Hiroyuki Saito to Masami Kitano. Further name of the patient of the room No. 605 is changed from Akiko Tachibana to Yoko Nakajima. This means that the two patients, Hiroyuki Saito and Akiko Tachibana are scheduled to be discharged from the hospital and the two patients, Masami Kitano and Yoko Nakajima are scheduled to be hospitalized by Mar. 23, 2014 which is three days later from today. Further, in this example, an asterisk (*) is displayed at the left side of the name of patient scheduled to be hospitalized so that a new inpatient can be recognized easily. Such the switching processing of the names of patients can be performed by the CPU 36 of the nurse call master unit 3, using the layout information and the information, contained in the patient information, which relates to scheduled discharging dates of patients and both scheduled hospitalization dates and room Nos. of patients scheduled to be hospitalized.

Further in the night shift zone on Mar. 23, 2014, two nurses (Ayako Terashima and Keiko Nakajima) are replaced by Yuko Hattori and Maki Hanai. Thus names of the three nurses, Mami Takada, Yuko Hattori and Maki Hanai are displayed on the layout screen 71A.

Concerning the names of six patients assigned to the nurse Mami Takada, it will be understood that three patients, that is, Masami Kitano and Shin Sato of the room No. 601 and Yoko Nakajima of the room No. 605, are added to the three patients (Tomoko Harada, Miki Aodoh, Satoru Kudo) having been assigned to this nurse on Mar. 20, 2014. Of these patients, Shin Sato of the room No. 605 is a patient assigned to the nurse Mami Takada serving as an assistant nurse. However as the nurse Ayako Terashima serving as a main nurse in charge of Shin Sato is absent at the night shift on March 23, Shin Sato is displayed as the patient assigned to the nurse Mami Takada. Further, concerning Masami Kitano of the room No. 601 and Yoko Nakajima of the room No. 605 each being the patient scheduled to be hospitalized, these patients are scheduled to be assigned to the nurse Mami Takada serving as a main nurse and hence applied with the hatching pattern 76a as the patients assigned to the nurse Mami Takada.

Further, each of Satomi Ueda of the room No. 602 and Tadahiko Kondo of the room No. 604 was assigned to the nurse Ayako Terashima serving as a main nurse and to the nurse Yuko Hattiri serving as an assistant nurse. Thus on the layout screen 71A, the names of these patients are applied with the hatching pattern 76b as the patients assigned to the nurse Yuko Hattori. Also, each of Taro Kato of the room No. 601 and Takashi Kitajima of the room No. 603 was assigned to nurse Keiko Nakajima serving as a main nurse and to the nurse Maki Hanai serving as an assistant nurse. Thus on the layout screen 71A, the names of these patients are applied with the hatching pattern 76c as the patients assigned to the nurse Maki Hanai. Incidentally if none of a main nurse and an assistant nurse in charge of a patient are absent, no hatching pattern may be applied to the inside of an indication frame surrounding name of this patient. Alternatively a hatching pattern indicating that all the nurses in charge are absent may be applied to the inside of this indication frame.

In this manner, the display switching of the hatching patterns indicating the nurses in charge, the numbers of patients assigned to the individual nurses and the nurses in charge at the next or succeeding (three days later in this case) working time zone (night shift in this case) can be performed by the CPU 36 of the nurse call master unit 3, using the working information of the individual nurses in charge, the person-in-charge information contained in the patient information for the individual patients and the layout information.

In this manner, concerning the layout screen 71A in this example, the names of patients and the names of nurses in charge of these patients at the next working time zone (night shift on Mar. 23, 2014) are simultaneously displayed on the large-sized monitor 31, in a display mode that the names of nurses are associated with the names of patients by the corresponding hatching patterns 76a to 76c.

The nurse manager can easily grasp visually, by looking at the layout screen 71A, that the nursing system (assignment of patients) at the night shift on Mar. 23, 2014, which is three days later from today, is unbalance in a nursing load as compared with the nursing system at the day shift on Mar. 20, 2014 shown in FIG. 4.

If the nurse manager understands from the layout screen 71A that the nursing load concentrates on the nurse Mami Takada, the nurse manager can change the patients assigned to the individual nurses and reorganize the nursing system, by performing touch operations on the large-sized monitor 31 which is configured by the touch panel and acts also as the operation part. Specifically, for example, the nurse manager changes the patient assigned to the nurse through such simple operations of touching the name of patient after touching the name of nurse, while looking at the screen 31.

Figure 6:
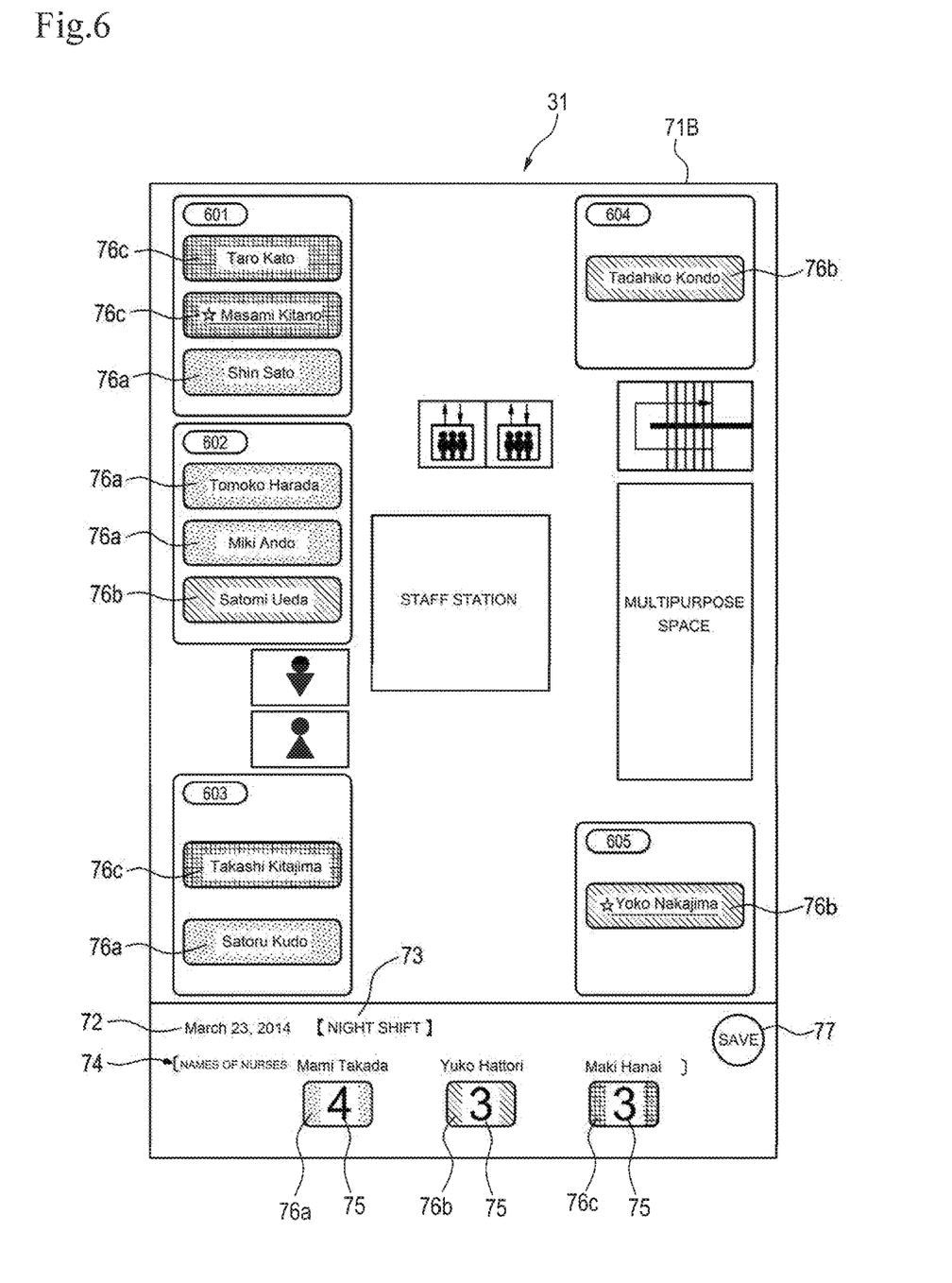
FIG. 6 A diagram illustrating an example of a layout screen after organizing a nursing system.

FIG. 6 shows a layout screen 71B at the night shift on Mar. 23, 2014 after the organization. From the comparison between the layout screen 71A (see FIG. 5) before the organization and the layout screen 71B after the organization, it will be understood that the nurse in charge of the patient Masami Kitano of the room No. 601 is changed from Mami Takada to Maki Hanai. Further the nurse in charge of Yoko Nakajima of the room No. 605 is changed from Mami Takada to Yuko Hattori. Specifically the name of nurse in charge of Masami Kitano is changed to Maki Hanai, and the kind of hatching pattern applied to Masami Kitano is changed to the hatching pattern 76c indicating the nurse Maki Hanai. Further the name of nurse in charge of Yoko Nakajima is changed to Yuko Hattori, and the kind of hatching pattern applied to Yoko Nakajima is changed to the hatching pattern 76b indicating the nurse Yuko Hattori. In this example, the nurse in charge of Masami Kitano of the room No. 601 is changed to the nurse Maki Hanai based on information that the nurse in charge of Taro Kato hospitalized in the room No. 601, which is the same room as that of Masami Kitano, is the nurse Maki Hanai.

As a result of this changing, the nursing load among the individual nurses is almost equalized in a manner that the number of patients assigned to the nurse Mami Takada is four, the number of patients assigned to the nurse Yuko Hattori is three and the number of patients assigned to the nurse Maki Hanai is three.

The nurse manager can save the new charge information (assignment of the patients to the corresponding nurses) by touching a save button 77 displayed on the layout screen 71B. For example, if the save button 77 is touched, the person-in-charge information after the organization is transmitted from the nurse call master unit 3 to the controller 5 via the controller I/F 37. The person-in-charge information after the organization transmitted to the controller 5 is inputted through the master unit I/F 54, and the person-in-charge information of the patient information stored in the patient information memory part 52a is updated by the person-in-charge information after the organization. Further the person-in-charge information after the organization is transmitted from the controller 5 to the ordering system 7 via the ordering I/F 56, and the patient information stored in a memory section of the ordering system 7 is updated by the person-in-charge information after the organization.

The nurse manager such as the chief nurse or the chief nursing officer organizes the individual nurses in charge of the patients and a nursing team in view of expertise of the individual nurses, substantial equalization of the nursing load, etc., thereby adjusting the nursing system in the entirety of hospital. However the number of inpatients changes depending on new inpatients and discharging patients due to complete recovery. Further condition of individual patients changes day by day. Thus the nurse manager is required to sequentially reconsider the nursing system according to change of a situation. For example, the nurse manager can reconsider the nursing system while confirming the patient information such as scheduled hospitalization day and previous symptom history for each new inpatient, utilizing the system as described in JP-A-2007-257351. However in the method utilizing such the system of the related art, the nursing system is merely reconsidered based on only the comparison of the patient information. When the number of patients increases, it becomes difficult to compare and consider the patient information of individual patients. As a result, there arises a case that the assignment of nursing load to the individual nurses becomes unintentional assignment, for example, insufficiently equalized assignment, and the nursing load concentrates on a particular nurse. Such the situation may badly influence on efficiency and quality of the nursing service.

In view of this fact, in the nurse call system 1 according to the embodiment, over the layout screen 71A relating to the next or succeeding working time zone prepared based on the working information and the layout information, the names of patients and the names of nurses in charge of these patients at the next working time zone are displayed simultaneously on the large-sized monitor 31, in the display mode that the names of nurses in charge of the patients are associated with the names of these patients by the corresponding hatching patterns 76a to 76c.

Thus, by looking at the layout screen 71A of the hospital rooms in the next or succeeding working time zone, the nurse manager can easily understand visually as to, for example, to which hospital room of which location a new patient is hospitalized, which nurse is scheduled to be in charge of the new patient, which nurse is in charge of a patient who is hospitalized near the new patient, and whether or not the numbers of patients assigned to the individual nurses are even. In this manner, according to the nurse call system 1, the nurse manager can easily understand visually unevenness of the assignment of nursing load supposed to occur in the future in a case of continuing the nursing under the current nursing system. As the unevenness of assignment of nursing load can be understood easily, the nurse manager can easily organize a new nursing system so that nursing loads applied to the individual nurses become almost even. As a result, efficiency and quality of the nursing service in the entirety of hospital can be improved.

Further, by looking at the layout screen 71A of the hospital rooms in the next or succeeding working time zone on the nurse call master unit 3, the nurse in charge can also easily understand the number of patients and a work load assigned to oneself in the working of near future.

Further the nurse call master unit 3 can change over the display between the layout screen 71 of the hospital rooms in the current working time zone and the layout screen 71 of the hospital rooms in the next or succeeding working time zone. By changing over the display between the current working time zone and the next or succeeding working time zone on the same layout screen 71, the comparison can be facilitated visually between an assignment state of the nursing load in the current working time zone and an assignment state of the nursing load in the next or succeeding working time zone. Thus the nurse manager can easily consider suitable organization of the nursing system according to change of the situation.

Further the nurse manager can change the nurses in charge of the patients by touching the touch panel screen of the large-sized monitor 31 while looking at the layout screen displayed on the large-sized monitor 31. Consequently an organization operation of reconsidering and organizing the nursing system can be facilitated.

According to the embodiment, by looking at the layout screen 71A indicating the layout of hospital rooms, the nurse manager can consider the nursing system in the next or succeeding working time zone so that the nursing loads of individual nurses become even also in view of the positional relation of the hospital rooms.

Next, explanation will be made as to another operation in a case where the layout screen 71A at the next or succeeding working time zone is displayed on the large-sized monitor 31 of the nurse call master unit 3.

For example, when the layout screen 71A at the next or succeeding working time zone, and so on are displayed on the large-sized monitor 31 of the nurse call master unit 3, the CPU 36 displays the current layout screen 71 (see FIG. 4) on the sub-monitor 35 in cooperation with the management PC 34.

By displaying the layout screen 71 at the current working time zone on the sub-monitor 35, the nurse manager can perform an organization operation of the nursing system at the next or succeeding working time zone on the large-sized monitor 31 of the nurse call master unit 3 while confirming the current nursing system by means of the layout screen 71 displayed on the sub-monitor 35.

Further, for example, if the call button of the nurse call slave unit 2 is pushed by a patient, a call signal outputted from the nurse call slave unit 2 is transmitted to the controller 5 via the corridor lamp 4. The controller 5 specifies the patient as an originator of this nurse call based on the call signal and the patient information, and transmits information specifying the patient to the nurse call master unit 3. In this case, if the layout screen 71A at the next or succeeding working time zone or the like is displayed on the large-sized monitor 31 of the nurse call master unit 3, the patient information of the patient as the caller is displayed on the small-sized monitor 32. In this case, for example, the bed No. name, etc. of this patient may also be displayed on the small-sized monitor 32.

In this manner, when the layout screen 71A at the next or succeeding working time zone or the like is displayed on the large-sized monitor 31 of the nurse call master unit 3, as the patient information of a patient originating a call from the nurse call slave unit 2 is displayed on the small-sized monitor 32, both a responding operation to the calling from the patient and an organization operation of the nursing system can be performed together.

As described above, by controlling the display contents of the sub-monitor 35 and the small-sized monitor 32, for example, each of the nurses can, in the staff station, respond to a calling from a patient using the small-sized monitor 32 while performing a meeting by seeing the sub-monitor 35. Further the nurse can perform the organization operation of nursing system on the large-sized monitor 31 of the nurse call master unit 3.

Next, a modified example of the screen displayed on the large-sized monitor 31 of the nurse call master unit 3 will be explained with reference to FIG. 7.

Figure 7:
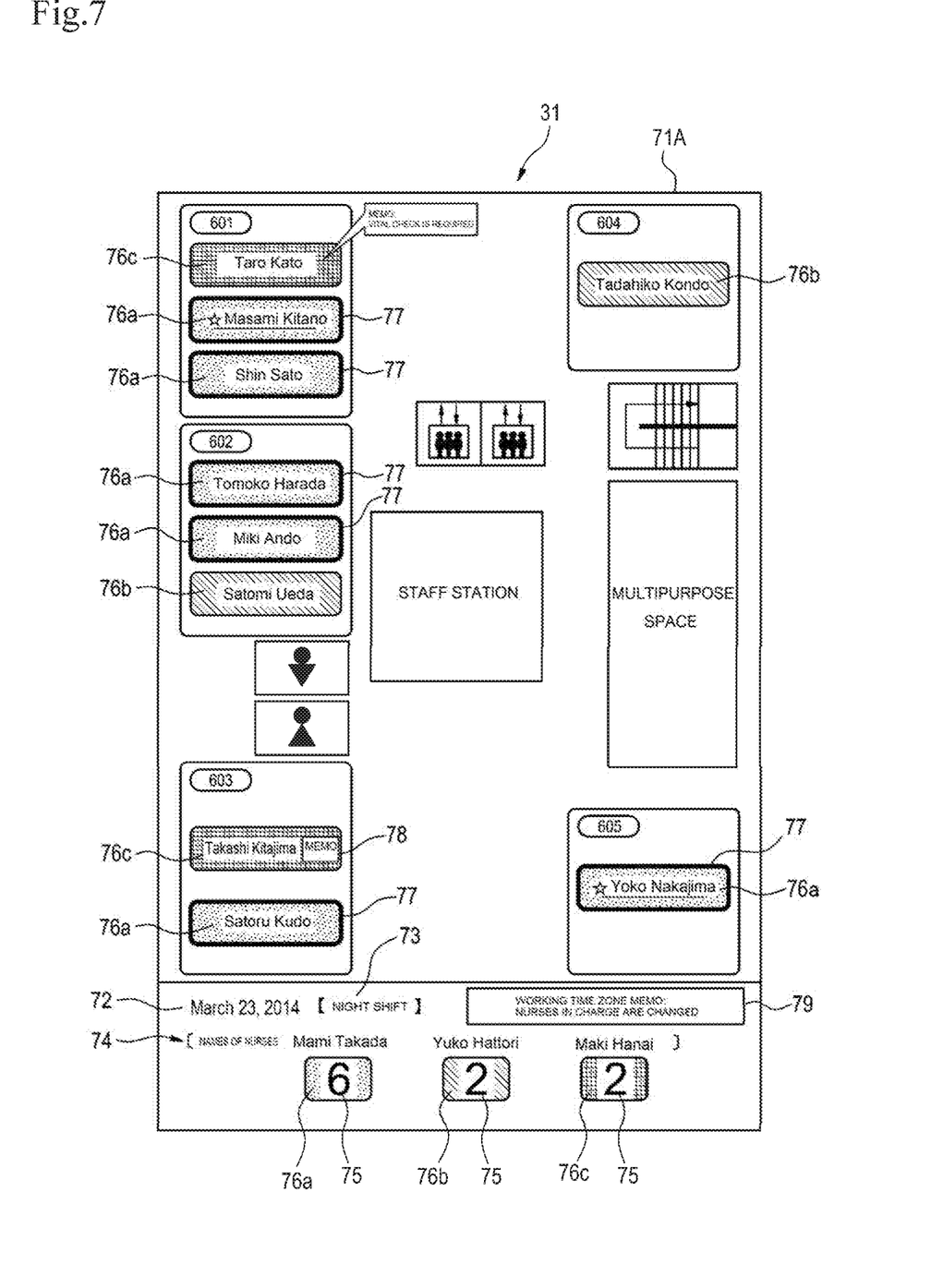
FIG. 7 A diagram for explaining a modified example.

FIG. 7 shows an example of a screen obtained by performing another additional processing on the layout screen 71A shown in FIG. 5.

As shown in FIG. 7, the CPU 36 of the nurse call master unit 3 displays, by a bold line, each of the indication frames of names of all patients assigned to the particular nurse selected through the touching operation or the like so as to enhance these names as compared with the other patients. In the example of FIG. 7, the nurse Mami Takada is selected, and so each of the indication frames of names of six patients assigned to the nurse Mami Takada, that is, Masami Kitano, Shin Sato, Tomoko Harada, Miki Ando, Satoru Kudo and Yoko Nakajima is displayed by a bold line 77.

In this manner, for example, at the time of considering the organization of nursing system, the nurse manager can perform the comparison operation further easily by highlighting each of the indication frames of names of patients assigned to the particular nurse. Thus the nurse manager can easily consider the assignment so that the assignment of the nursing load to the individual nurses at the next or succeeding working time zone becomes an intended arrangement, e.g., even arrangement. Incidentally the highlighting is not limited to the bold-line indication but may be another distinguishable indication mode such as a blinking indication.

Further as shown in FIG. 7, in a state where the layout screen 71A is displayed on the large-sized monitor 31, a particular patient may be selected by touching the name of this patient using, for example, a touch pen and further a patient memo concerning the selected patient may be inputted. The patient memo thus inputted may be recorded not only as information concerning the selected particular patient but also as information concerning all patients assigned to the nurse in charge of the selected patient. For example, in FIG. 7, if Taro Kato of the room No. 601 as one of patients assigned to the nurse Maki Hanai is selected and a patient memo (necessity of vital sign check) is inputted, this patient memo is also reflected on Takashi Kitajima of the room No. 603 as another patient assigned to the nurse Maki Hanai.

Consequently an operation of inputting the patient memo can be simplified and input omission of the memo can be prevented. Further, as the nurse manager can reconsider the current nursing system also in view of the contents of nurse memo, consideration of evenness or the like of the nursing load can be further facilitated. Incidentally this memo inputting function can also be applied to the current layout screen 71.

Further as shown in FIG. 7, inputting of a working time zone memo 79 at this working time zone may be made possible on the large-sized monitor 31. For example, in a state where the layout screen 71A of the next or succeeding working time zone (night shift on Mar. 23, 2014) is displayed, the working time zone memo is inputted by performing a touching operation or the like on the layout screen 71A. An example of the working time zone memo is a memo that "nurses in charge are changed" informing that the nurses in charge are changed due to resignation, for example.

The working time zone memo thus inputted is displayed only when the layout screen 71A at the night shift on Mar. 23, 2014, where the inputting operation is performed, is displayed.

Accordingly the nurse manager can reconsider the current nursing system also in view of the contents of working time zone memo.

The present invention is not limited to the embodiment described above and can be suitably modified and improved, for example. In addition, the material, shape, size, numerical value, mode, number, arrangement position, etc. of each of the constituent elements in the aforesaid embodiment are not particularly limited and may be set optionally so long as the invention can be achieved.

For example, in the aforesaid embodiment, although a main nurse and an assistant nurse are assigned to each of the patients, the invention is not limited thereto. For example, a plurality of (three, for example) nurses may be assigned to a single patient.

Further, in the aforesaid embodiment, although the working information is set with respect to each of the nurses, the invention is not limited thereto. For example, the nurses may be divided into a plurality of nurse teams, and the nurse teams and the patients may be displayed simultaneously on the layout screen in a manner that each of the patients is associated with one of the nurse teams, on the nurse team unit basis.

Further, in the aforesaid embodiment, although the explanation is made as to the case where the patient and working information is periodically transmitted from the ordering system 7 and stored in the patient information memory part 52a and the working information memory part 52b, respectively, the invention is not limited thereto. For example, in a configuration not installing the ordering system 7, the individual information may be directly inputted into the nurse call master unit 3 and the controller 5. Further in a case where the individual information is partially updated, the nurse call system 1 is merely required to reflect the updated contents on the memory parts storing the similar information. The gist of the present invention is not limited by where in the constituent elements the individual memory parts are located, or by where in the memory parts the individual information is stored, or by information stored in which memory parts being to be used to realize the present invention.

Although the present invention is explained in detail with reference to the particular embodiment, it will be apparent for those skilled in the art that various changes and modifications are possible without departing from the spirit and range of the present invention.

This application is based on Japanese Patent Application No. 2014-065925 filed on Mar. 27, 2014, the content of which is incorporated herein by reference.

DESCRIPTION OF REFERENCE NUMERALS

1: nurse call system, 2 (2a, 2b, 2c, 2d): nurse call slave unit, 3: nurse call master unit, 4 (4a, 4b): corridor lamp, 5: controller, 6 (6a, 6b, 6c, 6d): mobile terminal, 7: ordering system, 31: large-sized monitor (an example of first display part), 32: small-sized monitor (an example of second display part), 35: sub-monitor (an example of third display part), 36: CPU (an example of display control unit), 38: memory section, 51: CPU, 52: memory section, 52a: patient information memory part, 52b: working information memory part, 52c: layout information memory part, 71, 71A, 71B: layout screen, 72: date, 73: working time zone

The invention claimed is:

1. A nurse call system, comprising:
a nurse call master unit which includes a first display part;
a patient information memory unit which stores patient information containing at least names of patients, person-in-charge information representing nurses each in charge of one or more of the patients, and hospital room information of the individual patients;
a working information memory unit which stores working information of the nurses for each day and each working time zone;
a display control unit which displays a plurality of the patients and the nurses each in charge of one or more of the plurality of patients in a next or succeeding working time zone simultaneously on the first display part, in a display mode of associating each of the plurality of patients with one of the nurses, based on the patient information and the working information; and
a layout information memory unit for storing layout information of individual hospital rooms in a predetermined area of a hospital,
wherein the nurse call master unit comprises a touching operation to distinguish one or more of the names of the nurses by an indicator, wherein the indicator includes highlighting or blinking,
wherein the nurse call master unit includes an operation part for selecting the patient information of a particular one of the patients and input a patient memo, in the state where the plurality of patients and the nurses each in charge of one or more of the plurality of patients in the next or succeeding working time zone are simultaneously displayed on the first display part, in the display mode of associating each of the plurality of patients with one of the nurses, and
wherein the patient memo appears within the patient information of all of the other patients assigned to the nurse in charge of the particular patient,
wherein the display control unit displays:
a layout screen indicating a layout of the individual hospital rooms in the predetermined area of the hospital on the first display part based on the layout information, and
based on the patient information and the working information, the plurality of patients, the nurses each in charge of one or more of the plurality of patients, and the hospital rooms for the plurality of patients in the next or succeeding working time zone simultaneously over the layout screen on the first display part, in the display mode of, and
wherein, in the display mode, a common hatching pattern is applied to inside of an indication frame surrounding the name of the patient and to inside of an indication frame surrounding the number of the patients assigned to the nurse.

2. The nurse call system according to claim 1, wherein the operation part can change the nurse in charge of the patient displayed on the first display part, in a state where the plurality of patients and the nurses each in charge of one or more of the plurality of patients in the next or succeeding working time zone are simultaneously displayed on the first display part, in the display mode of associating each of the plurality of patients with one of the nurses.

3. The nurse call system according to claim 1, wherein the patient information memory unit stores patient information of patients now being hospitalized and patient information of patients scheduled to be hospitalized.

4. The nurse call system according to claim 1, wherein the display control unit can emphatically display the patient information of a patient assigned to a particular one of the nurses, in a state where the plurality of patients and the nurses each in charge of one or more of the plurality of patients in the next or succeeding working time zone are simultaneously displayed on the first display part, in the display mode of associating each of the plurality of patients with one of the nurses.

5. The nurse call system according to claim 1, further comprising:
a nurse call slave unit which can communicate with the nurse call master unit, wherein
the nurse call master unit includes a second display part, and wherein
the display control unit displays the patient information of one of the patients, who is calling from the nurse call slave unit, on the second display unit, in a state where the plurality of patients and the nurses each in charge of one or more of the plurality of patients in the next or succeeding working time zone are simultaneously displayed on the first display part, in the display mode of associating each of the plurality of patients with one of the nurses.

6. The nurse call system according to claim 1, further comprising:
a display unit which can communicate with the display control unit and includes a third display part that is physically separate from the first display part, wherein
the display control unit can display a plurality of the patients and the nurses each in charge of one or more of the plurality of patients in a current working time zone simultaneously on the third display part in a display mode of associating each of the plurality of patients with one of the nurses, in a state where the plurality of patients and the nurses each in charge of one or more of the plurality of patients in the next or succeeding working time zone are simultaneously displayed on the first display part in the display mode of associating each of the plurality of patients with one of the nurses.

7. The nurse call system according to claim 2, wherein the operation part can input a working time zone memo with respect to information displayed on the first display part, in the state where the plurality of patients and the nurses each in charge of one or more of the plurality of patients in the next or succeeding working time zone are simultaneously displayed on the first display pan, in the display mode of associating each of the plurality of patients with one of the nurses, and the working time zone memo is displayed on the first display part only in the state where the plurality of patients and the nurses each in charge of one or more of the plurality of patients in the next or succeeding working time zone are simultaneously displayed on the first display part, in the display mode of associating each of the plurality of patients with one of the nurses.

8. The nurse call system according to claim 6, further comprising;
wherein the operation part can change one or more of the nurse in charge in the next or succeeding working time zone of one or more patients displayed on the first display part, while the display control unit simultaneously displays the plurality of the patients and the nurses each in charge of one or more of the plurality of patients in the current working time zone on the third display part,
wherein the display unit updates the common hatching pattern applied to inside of the indication frame surrounding the name of the patient and to inside of an indication frame surrounding the number of the patients assigned to the nurse in response to the change of one or more of the nurse in charge in the next or succeeding working time zone of one or more patients displayed on the first display part.

* * * * *